(12) United States Patent
Albarano

(10) Patent No.: US 12,178,900 B2
(45) Date of Patent: Dec. 31, 2024

(54) PHARMACEUTICAL COMPOSITIONS

(71) Applicant: JOYDERMA AG, Eich (CH)

(72) Inventor: Teo Albarano, Eich (CH)

(73) Assignee: JOYDERMA AG, Eich (CH)

( * ) Notice: Subject to any disclaimer, the term of this patent is extended or adjusted under 35 U.S.C. 154(b) by 229 days.

(21) Appl. No.: 17/523,661

(22) Filed: Nov. 10, 2021

(65) Prior Publication Data
US 2022/0124572 A1 Apr. 21, 2022

Related U.S. Application Data

(63) Continuation of application No. 16/496,291, filed as application No. PCT/EP2018/057416 on Mar. 23, 2018, now abandoned.

(30) Foreign Application Priority Data

Mar. 24, 2017 (CH) .......................... 386/17

(51) Int. Cl.
A61K 8/73 (2006.01)
A61K 8/14 (2006.01)
(Continued)

(52) U.S. Cl.
CPC ............... *A61K 8/735* (2013.01); *A61K 8/14* (2013.01); *A61K 8/347* (2013.01); *A61K 8/63* (2013.01);
(Continued)

(58) Field of Classification Search
None
See application file for complete search history.

(56) References Cited

U.S. PATENT DOCUMENTS

2007/0077292 A1 4/2007 Pinsky
2007/0110731 A1 5/2007 Riley
(Continued)

FOREIGN PATENT DOCUMENTS

EP 2570 118 A1 3/2013
EP 2 893 935 A1 7/2015
(Continued)

OTHER PUBLICATIONS

Dua et al. "Liposome: Methods of preparation and applications", International Journal of Pharmaceutical Studies and Research, April-June, 14-20 (Year: 2012).*
(Continued)

*Primary Examiner* — Isis A Ghali
(74) *Attorney, Agent, or Firm* — Pauley Erickson & Swanson

(57) ABSTRACT

A composition including a synergistic combination of a vitamin D3 or a derivative or precursor thereof and hyaluronic acid or derivate thereof encapsulated in a lipid based colloidal carrier system (preferably lipid based vesicles such as liposomes, niosomes, tranferosomes) and topical formulations thereof, as well as their use in the prevention and/or treatment of inflamed skin and mucous membrane, especially in the prevention and/or treatment of skin photodamage, in particular in the prevention and/or treatment of skin erythema (skin inflammation) and actinic keratosis, as well non melanoma skin cancer.

20 Claims, 3 Drawing Sheets

(51) Int. Cl.
    *A61K 8/34*         (2006.01)
    *A61K 8/63*         (2006.01)
    *A61Q 17/04*       (2006.01)
    *H04W 36/00*      (2009.01)
    *H04W 74/0833*    (2024.01)

(52) U.S. Cl.
    CPC ........ *A61Q 17/04* (2013.01); *H04W 36/0058* (2018.08); *H04W 74/0833* (2013.01)

(56) References Cited

U.S. PATENT DOCUMENTS

| | | | |
|---|---|---|---|
| 2008/0145415 A1* | 6/2008 | Callegaro | A61K 31/715 514/54 |
| 2008/0233183 A1* | 9/2008 | McCook | A61K 47/34 424/94.1 |
| 2011/0262505 A1 | 10/2011 | Athwal | |
| 2012/0058061 A1 | 3/2012 | Nguyen et al. | |
| 2012/0128777 A1 | 5/2012 | Keck et al. | |
| 2012/0201871 A1 | 8/2012 | Banov et al. | |
| 2013/0149385 A1 | 6/2013 | Mousa | |
| 2017/0079900 A1 | 3/2017 | Pinna et al. | |
| 2020/0046627 A1 | 2/2020 | Albarano | |

FOREIGN PATENT DOCUMENTS

| | | |
|---|---|---|
| JP | 2004-175731 A | 6/2004 |
| JP | 2008-540514 A | 11/2008 |
| WO | WO 2006/120682 A2 | 11/2006 |

OTHER PUBLICATIONS

Gonnet et al. "New trends in encapsulation of liposoluble vitamins", Journal of Controlled Release, 146, 276-290 (Year: 2010).*

Japanese Patent Office, English Translation of Japanese Office Action and Search Results for Japanese Patent Application No. 2020-501595, Nov. 9, 2021 (8 pp.).

Weindl et al., "Hyaluronic Acid in the Treatment and Prevention of Skin Diseases: Molecular Biological, Pharmaceutical and Clinical Aspects," Skin Pharmacology and Physiology; Journal of Pharmacological and Biophysical Rese, S. Karger AG, Basel, CH, vol. 17, Jan. 1, 2004, pp. 207-213.

Haes et al.,"1,25-Dihydroxyvitamin D3 and analogues protect primary human keratinocytes against UVB-induced DNA damage," Journal of Photochemistry and Photobiology B: Biology, Elsevier Science S.A., Basel, CH, vol. 78, No. 2, Feb. 1, 2005, pp. 141-148.

* cited by examiner

PHARMACEUTICAL COMPOSITIONS

CROSS REFERENCE TO RELATED APPLICATION

This application is a continuation of U.S. application Ser. No. 16/496,291, filed on 20 Sep. 2019. The co-pending parent application is hereby incorporated by reference herein in its entirety and is made a part hereof, including but not limited to those portions which specifically appear hereinafter.

BACKGROUND OF THE INVENTION

Field of the Invention

The present invention is directed towards new compositions comprising a synergistic combination of a vitamin D or a derivative or precursor thereof and hyaluronic acid or derivate thereof encapsulated in a lipid based colloidal carrier system (preferably lipid based vesicles such as liposomes, niosomes, tranferosomes) and topical formulations thereof, as well as their use in the prevention and/or treatment of inflamed skin and mucous membrane, especially in the prevention and/or treatment of skin photodamage, in particular in the prevention and/or treatment of skin erythema (skin inflammation) and actinic keratosis, as well non melanoma skin cancer.

Discussion of Related Art

Skin disorders according to ICD-10 (International Classification of Diseases, Version 2016) include (a) group of conditions in which the skin becomes inflamed, forms blisters, and becomes crusty, thick, and scaly (including eczema causing burning and itching, occurring over a long period of time), (b) any type of skin inflammation, (c) an inflammatory process affecting the skin (with signs of red rash, itching, and blister formation), e.g. contact dermatitis, atopic dermatitis, seborrheic dermatitis and psoriasis, and (d) pruritic papulovesicular dermatitis occurring as a reaction to many endogenous and exogenous agents. Photo damage of the skin (according to ICD-10 version 2016) is characterized as a skin disorder due to radiation of ultraviolet A (UVA) and ultraviolet B (UVB) with the following major symptoms: skin atrophy, skin dyspigmentation (patches/spots), photodermatitis (erythema: inflamed, reddened skin), telangiectasia, (couperose) and actinic keratosis. UVB with a wavelength of 280-315 nm provides the energy the skin needs to make vitamin D3, but is also a primary mutagen that penetrates through the epidermal layer of the skin, resulting in DNA mutations, potentially leading to skin cancer (non melanoma skin cancer (NMSC) and melanoma). These mutations may be clinically related to specific signs of photodamage such as increasing in elastin and collagen defects resulting in skin atrophy. UVA with a wavelength of 315-400 nm is able to penetrate deeper into the skin as compared to UVB rays and thus may damage both the epidermal and dermal layers. With constant UVA exposure, the size of the dermis layer will be reduced, causing an atrophy of the skin. Potential damages include dilated or broken blood vessels, causing telangiectasia (couperose) or indirect damages to cellular DNA as well as lipids and proteins of the skin barrier through the generation of reactive oxygen species (ROS), which are cytotoxic. Both UVA and UVB exposure can also lead to inflammation and vasodilation, which is clinically manifested as telangiectasia, (couperose) and photodermatitis (erythema resulting in inflamed and reddened skin), Dyspigmentation (patches/spots) and other skin disorders [see e.g. 1, 2, 3].

In inflamed skin tissue high concentrations of reactive oxygen species (ROS) like nitric oxide are present. Nitric oxide (NO) reacts further with oxygen ($O_2$) to peroxynitrite ($ONOO^-$). Peroxynitrite and its degradation from the reaction with $CO_2$ ($NO_2^-$ and $CO_3^-$) are highly cytotoxic throughout the oxidation of lipids, proteins and DNA in the epidermis.

Various approaches have been suggested to counter skin inflammations such as photodamage and its effects, including the uses of vitamins, for example vitamin D3 and its derivatives and precursors, as well as hyaluronic acid and the like.

Vitamin D is a group of fat-soluble vitamins with vitamin $D_3$ (or cholecalciferol) and vitamin $D_2$ (or ergocalciferol) being the most important representatives in humans. Typically, vitamin D3 is obtained by photolysis of 7-dehydrocholesterol (or 7-DHC, found prominently in the stratum spinosum and stratum basale of the upper layer of the skin at about 25-50 ug/cm$^2$) by UVB [see e.g. 4-7, FIG. 1] to obtain the precursor previtamin D3, which is then thermally isomerized to give vitamin D3. It is known that the vitamin D3 production throughout the skin decreases dramatically with aging (up to 75 wt % at the age of 70). Vitamin D3 and its precursors and derivatives are biologically very active. For example, the precursor 7-DHC has the capability to bind the reactive oxigenes species NO and thus avoids overproduction of cytotocic peroxynitrite in the upper parts of the skin, preventing the vicious circle (circulus vitiosus) of skin inflammation with cellular skin damages [FIGS. 2, 3]. Vitamin D3 plays a role in many processes, including bone mineralization, bone growth and bone remodelling, modulation of cell growth, neuromuscular and immune function, and others. It has also been proposed that certain vitamin D3 analogues (e.g. 25-hydroxy-vitamin-D3 or calcidiol, 1,25-dihydroxyvitamin-D3 or calcitriol, calcipotriol; see e.g. 8, 9, 10, FIG. 3) can be used topically to treat skin conditions, including psoriasis [see e.g. 11, 12, 13, 14]. In addition, recent studies using genetically modified mice, which exhibit altered mineral homeostasis due to a high vitamin D3 activity, showed features of premature aging that include retarded growth, osteoporosis, atherosclerosis, ectopic calcification, immunological deficiency, skin and general organ atrophy. This and other findings suggests that serum calcidiol might be associated with an increased risk of aging-related chronic diseases including cancer. Vitamin D is also involved in rebuilding the skin barrier [see e.g. 15, FIG. 2], sustaining immune defence against microorganisms and protecting a healthy microflora [see e.g. 16], Vitamin D3 also reduce inflammation, supporting of the skin and is involved in the wound healing [see e.g. 17-20], and protecting the skin from photo damage [see e.g. 21-25, FIGS. 2, 3]. It is presumed that throughout the local production of vitamin D in the skin together with the skin browning is the most important mechanism of skin protection against photo damage [see e.g. 26].

Hyaluronic acid (HA) is a linear polysaccharide with repeating disaccharide units composed of glucuronic acid and N-acetyl glucosamine and is one of the major matrix substances in which cells and fibrous constituents of the matrix such as collagen and elastin are embedded [see e.g. 27, 28, FIG. 2]. HA has an enormously high water binding capacity [see e.g. 29] and contributes largely to the maintenance of the extracellular space and to control tissue hydration working as a humectant [see e.g. 30]. It is known, that crosslinking HA polymer chains transform the HA solution into a gel. Crosslinker molecules bind individual HA polymer chains to create a network, which manifests macroscopically as a gel mass. It has been suggested that HA plays a pivotal role in tissue regeneration [see e.g. 31, 32, FIG. 2].

However, despite the numerous formulations that are commercialized for skin treatments, there is still a high need for a formulation that is capable to prevent and/or treat the common symptoms of skin inflammation, especially photodamage, namely the affected skin and even more to prevent skin damages caused by sun exposure, especially by UV radiation, with greater effectiveness.

Applicants have now found that vitamin D3 or a derivative or precursor thereof, preferably a precursor such as 7-dehydrocholesterol (7-DHC) or a derivative thereof can be formulated in combination with HA as a stabilized colloid. This colloidial carrier system shows a synergistic effect in the treatment and prevention of inflamed skin, especially photodamage of the skin, such as skin atrophy, skin dyspigmentation (patches/spots), photodermatitis (erythema: inflamed and reddened skin), telangiectasia, (couperose) and UV prevention to avoid skin erythema and actinic keratosis [FIG. 2].

Thus applicants provide a new composition comprising vitamin D3 or a derivative or precursor thereof, preferably a precursor such as 7-DHC or a derivative thereof and HA or derivatives, optionally in combination with additional excipients, encapsulated in a lipid based colloidal carrier system (preferably lipid based vesicles such as liposomes, niosomes, tranferosomes) to allow the penetration and localized delivery of stabilized vitamin D3 or a derivative or precursor thereof, preferably a precursor such as 7-DHC or a derivative thereof into the upper layers of the skin.

The two active substances combined topically are able to act in a synergistic manner directly in the upper layers of the skin on the dominant disorders of inflamed skin, especially in photodamage, in particular on the indication according ICD-10 of sun and especially UV radiation exposed and damaged skin. Thus the new composition of the invention is able to overcome drawbacks of prior art. The additional seven excipients will act synergistic with the two active substances and allow an optimal efficacy to prevent and/or treat the described skin disorders. The described composition (and formulations thereof) will provide a new approach to prevent and/or treat most disorders of inflamed skin, sun and especially UV radiation damaged skin [FIGS. 2, 3].

SUMMARY OF THE INVENTION

In a first aspect, the invention is directed towards a new composition (also referred to as composition of the invention) comprising a synergistic combination of at least one vitamin D3 or a derivative or precursor thereof, preferably a precursor such as 7-DHC or a derivative thereof and at least one HA or derivative thereof, encapsulated in a lipid based colloidal carrier system (to allow for optimal skin penetration and stabilization of the vitamin D3 or a precursor or derivative thereof) and suitable formulations thereof. By encapsulation in the oil (or lipid) phase the vitamin D3 or a precursor or derivative thereof (and in particular 7-DHC or a derivative thereof) is stabilized and undesired reactions (such as oxidation or other degradation reactions) are eliminated. The lipid based colloidal carrier system allows vitamin D3 (and inactive vitamin D3 precursors such as 7-DHC or a derivative thereof) to penetrate into the upper layers of the skin, where exerts its activity (after being converted into the active vitamin D3 upon UVA and UVB exposure).

In a preferred embodiment the vitamin D3 is a vitamin D3 precursor such as 7-DHC or a derivative thereof, and the composition of the invention comprises a vitamin D precursor such as 7-DHC or a derivative thereof, in combination with HA or a derivative thereof encapsulated in a lipid based colloidal carrier system. The vitamin D (and in particular the vitamin D3 precursor such as 7-DHC or a derivative thereof) is preferably present in the colloidal carrier system at a final concentration of 0.01 to 0.5 wt %.

In other embodiments the composition further comprises one or more, preferably 1, 2, 3, 4, 5, 6, 7 further components selected from a vitamin A (preferably retinyl palmitate), at least one vitamin B, a vitamin C (preferably L-ascorbic acid) and a vitamin E (preferably tocopheryl acetate). Preferably, the composition further comprises one or more, most preferably all, of (i) retinyl palmitate (vitamin A), (ii) riboflavin (vitamin B2), (iii) niacinamide (vitamin B3), (iv) dexpanthenol (Provitamin B5), (v) folic acid (vitamin B9), (vi) L-ascorbic acid (vitamin C) and (vii) tocopheryl acetate (vitamin E).

In another specific embodiment, the lipid based colloidal carrier system is a liposomal carrier system (preferably a lipid based vesicle such as liposome, niosome, tranferosome) composed of at least one phospholipid and at least one fatty acid. Preferably the lipid based colloidal carrier system comprises one or more of e.g. lecithin, linolenic acid, linoleic acid, phosphatidylcholine and caprylic/capric triglyceride.

In a preferred embodiment, the lipid based colloidal carrier (e.g. a lipid based vesicle such as liposome, niosome, tranferosome) comprises the synergistic combination of 7-DHC and HA in combination with the two lipophilic agents retinyl palmitate (Vitamin A), tocopheryl acetate (Vitamin E), and the five hydrophilic agents riboflavin (Vitamin B2), niacinamide (Vitamin B3), dexpanthenol (Provitamin B5), folic acid (Vitamin B9), L-ascorbic acid (Vitamin C).

The lipophilic agents are encapsulated within the bilayer or multilamellar system, whereas the hydrophilic agents are encapsulated in the aqueous phase. Thus, in one embodiment the composition of the invention is obtained by (i) encapsulating the vitamin D3 (and in particular vitamin D3 precursor such as 7-DHC or a derivative thereof) in the oil (or lipid) phase of the lipid based colloidal carrier system at room temperatures, and (ii) separately preparing HA in the aqueous phase. The compositions are obtained by emulsification of the water phase with the oil (or lipid) phase (by mixing or spontaneous integration at room temperature). Preferably, the particles will have a diameter of 10-500 nm, more preferably 10-300 nm, most preferably 20-150 nm.

In a further aspect, the composition of the invention is in form of various formulations suitable for topical or transdermal and mucosa administration. These topical formulations contain the pharmaceutical composition of the invention, as well as further auxiliary agents, such as buffering agents, preserving agents and the like. Typical formulations include hydrogels, liogels, hydrolotions, lipolotions, crèmes, ointments, and the like.

In a further aspect, the invention is directed towards the use of the composition of the invention (and topical formulations thereof) in the prevention and/or treatment of skin photo damage symptoms, in particular in the prevention and/or treatment of skin atrophy, skin dyspigmentation (patches/spots), photodermatitis (erythema: inflamated and reddened skin), telangiectasia, (couperose), prevention of photodermatitis (erythema: inflammation of the skin), actinic keratosis and skin UVA and UVB protection.

DETAILED DESCRIPTION OF THE INVENTION

Figure 1:
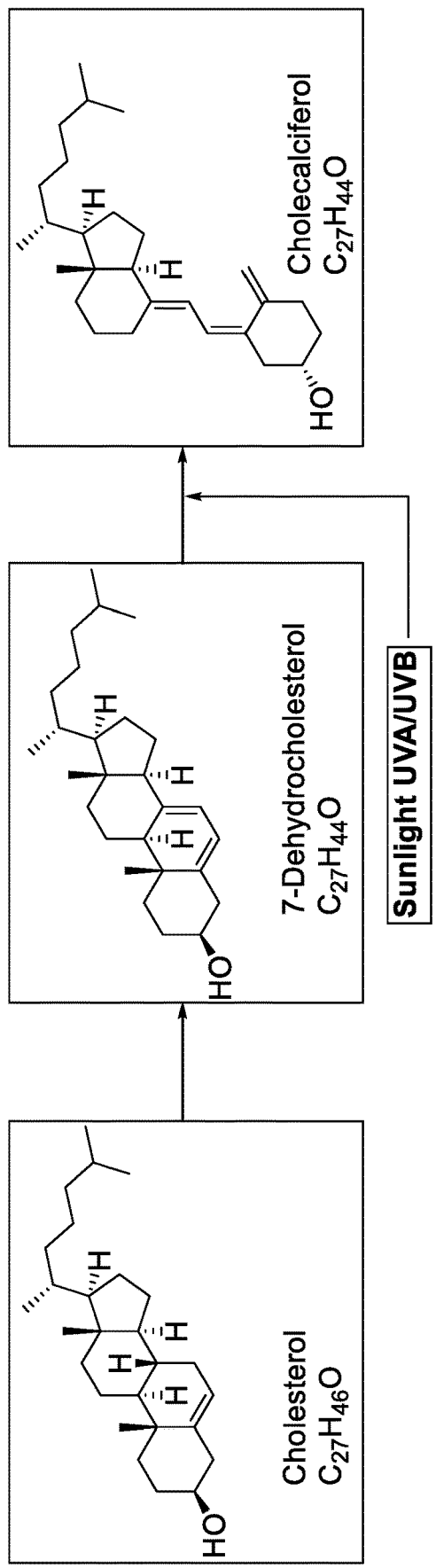
FIG. 1: Adequate concentrations of the inactive precursor 7-DHC is transported in form of a lipid-based colloid according to the invention in the upper layers of the skin, where it is converted to active vitamin D3 upon UVA and UVB exposure.

In a first aspect, the invention is directed towards a new composition, hereinafter also called composition of the invention, comprising a synergistic combination of at least one vitamin D3 or a precursor or derivative thereof, preferably a precursor such as 7-dehydrocholesterol (7-DHC) or a derivative thereof, and at least one HA or derivative thereof, encapsulated in a lipid based colloidal carrier system (preferably lipid based vesicles such as liposomes, niosomes, tranferosomes), and suitable topical formulations thereof. All definitions and embodiments specified hereinafter apply to the compositions (and topical formulations) of the invention and uses thereof (unless specified otherwise). The term "topical" as used herein refers to administration to any part of the skin and mucous membranes, including ocular mucous membranes. The term "photodamage" as used herein refers to ICD-10 definition 2016 and is characterized as a skin disorder due to sun exposure and to radiation of UVA and UVB. The term "synergistic" when used in relation to the compositions of the present invention means that the therapeutic effect of the combination of agents is greater than the sum of the effects of the individual agents in the combination.

The term "vitamin D" as used herein refers to any of the antirachitic forms known in the art to be suitable for nutritional use such as vitamin $D_1$, vitamin $D_2$, vitamin $D_3$, vitamin $D_4$, vitamin $D_5$, vitamin $D_6$, and vitamin $D_7$. Preferred is "vitamin D3", which as used herein refers to vitamin D3 as well as a precursor of vitamin D3, such as 7-DHC (provitamin D3) or a derivative thereof, or a derivative of vitamin D3, such as 25-hydroxyvitamin D3, or 1a, 25-dihydroxyvitamin D3, including, 1a-hydroxyvitamin D3, that activates the vitamin D receptor or that can be metabolically converted in a human to a compound that activates the vitamin D receptor. Preferred is 7-DHC. The vitamin D, preferably the vitamin D3 and its precursor 7-DHC, is used at a concentration of 10,000 IU-50,000 IE and 0.01-4 wt %. Preferable concentration of 0.01 to 3 wt %, more preferably of 0.01 to 0.75 wt %, most preferably 0.01 to 0.5 wt % of the total weight of the composition according to the present invention.

The term "hyaluronic acid" (also known as hyaluronan, hyaluronate, or HA) as used herein refers to an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. The term "hyaluronic acid" or "HA" as used in the present application refers to HA or salts of HA, such as the sodium, potassium, magnesium and calcium salts, among others. The term "hyaluronic acid" or "HA" includes both natural and synthetic formulas and combinations of these natural and synthetic formulas including salt forms thereof. HA and its various molecular size fractions and the respective salts thereof have been used as medicaments, especially in treatment of arthropathies, as an auxiliary and/or substitute agent for natural organs and tissues, especially in ophthalmology and cosmetic surgery, and as agents in cosmetic preparations. Products of HA have also been developed for use in orthopaedics, rheumatology, and dermatology. High molecular weight (MW) fractions of HA having an average MW of about 1 to about 1.5 MDa are well known for providing excellent moisturizing properties in cosmetic compositions such as lotions and creams. Very low MW fractions of HA have been reported to have a higher ability to penetrate the skin barrier. In preferred embodiments, a crosslinking agent (e.g. 1,4-butanediol diglycidal ether (BDDE) and the like) can be used to bind HA polymer chains to each other, transforming liquid HA solutions into gels. Thus, in a specific embodiment, HA is in form of a gel obtained by crosslinking the HA polymer chains (through the primary hydroxyl site (—$CH_2OH$) and/or secondary hydroxyl sites (—CHOH) within the HA monomeric unit), with low molecular crosslinked HA showing a high water retention capacity into the skin. HA for use in the present invention is preferably of low MW, e.g. 4 kDa to 50 kDa, combined with higher MW up to 200'000 kDa. Typically, the HA is used at a concentration of 0.01 to 8 wt % (or 80 mg/ml), preferably of 0.01 to 5 wt % (or 50 mg/ml), more preferably of 0.01 to 4 wt % (or 40 mg/ml), most preferably 0.01 to 3 wt % (or 30 mg/ml). The most preferable concentration of total HA is 3 wt %, preferably as a mixture of lowest MW HA of 4-5 kDa, low to medium or medium molecular HA of 40-50 kDa and high MW HA of 50'000-200'000 kDa (wt %). Preferably the ratio of lowest molecular HA of 4-5 kDa to medium molecular HA of 40-50 kDa to high MW HA of 50'000-200'000 kDa is (1-10):(0.1-2):(0.1-2), preferably (2-6):(0.5-1.5):(0.5-1.5), most preferably about 4:about 1:about 1 (or about equal wt % of medium and highMW HA). Thus, most preferred is as a 3 wt % HA mixture of 2 wt % of lowest molecular HA of 4-5 kDa, 0.5 wt % of low to medium or medium molecular HA of 40-50 kDa and 0.5 wt % of high MW HA of 50'000-200'000 kDa.

Figure 2:
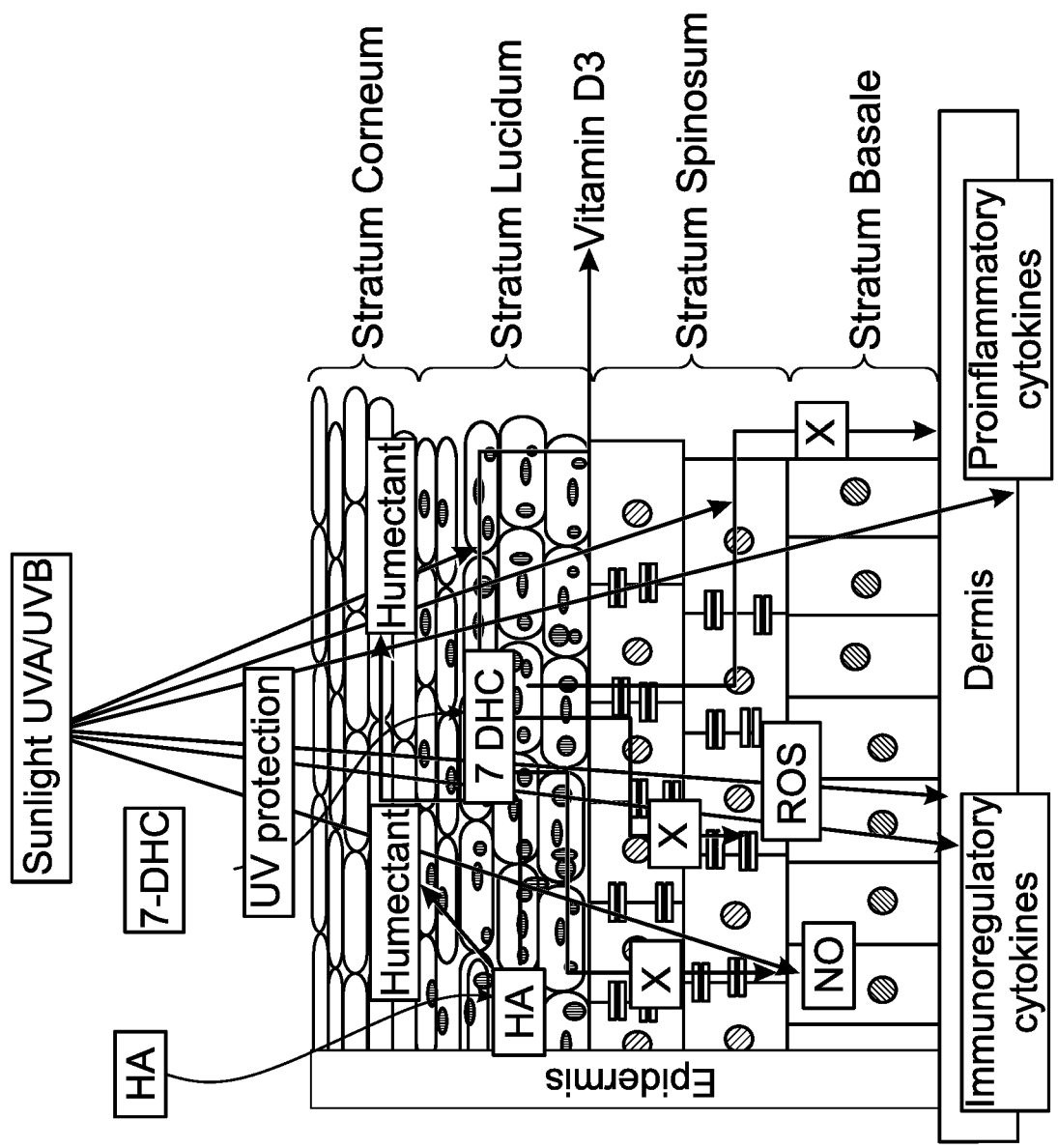
FIG. 2: 7-DHC in the oil (or lipid) phase and hyaluronic acid (HA) in the water phase are integrated into the colloidal carrier system, which allows the penetration into the upper layers of the skin. With the activation and synthesis of vitamin D3 from 7-DHC the pathway of skin damages by sunlight UVA/UVB can be blocked. Inactive 7-DHC is protected from oxidative processes with the encapsulation into the carrier system and further being only activated at the target into the upper layers of the skin having a potent function eliminating cytotoxic ROS as peroxynitrates, resulting from the oxidative processes of nitrates. This scavenger function of in excess produced NO's allows the protection of skin damages from UVA/UVB.
Figure 3:
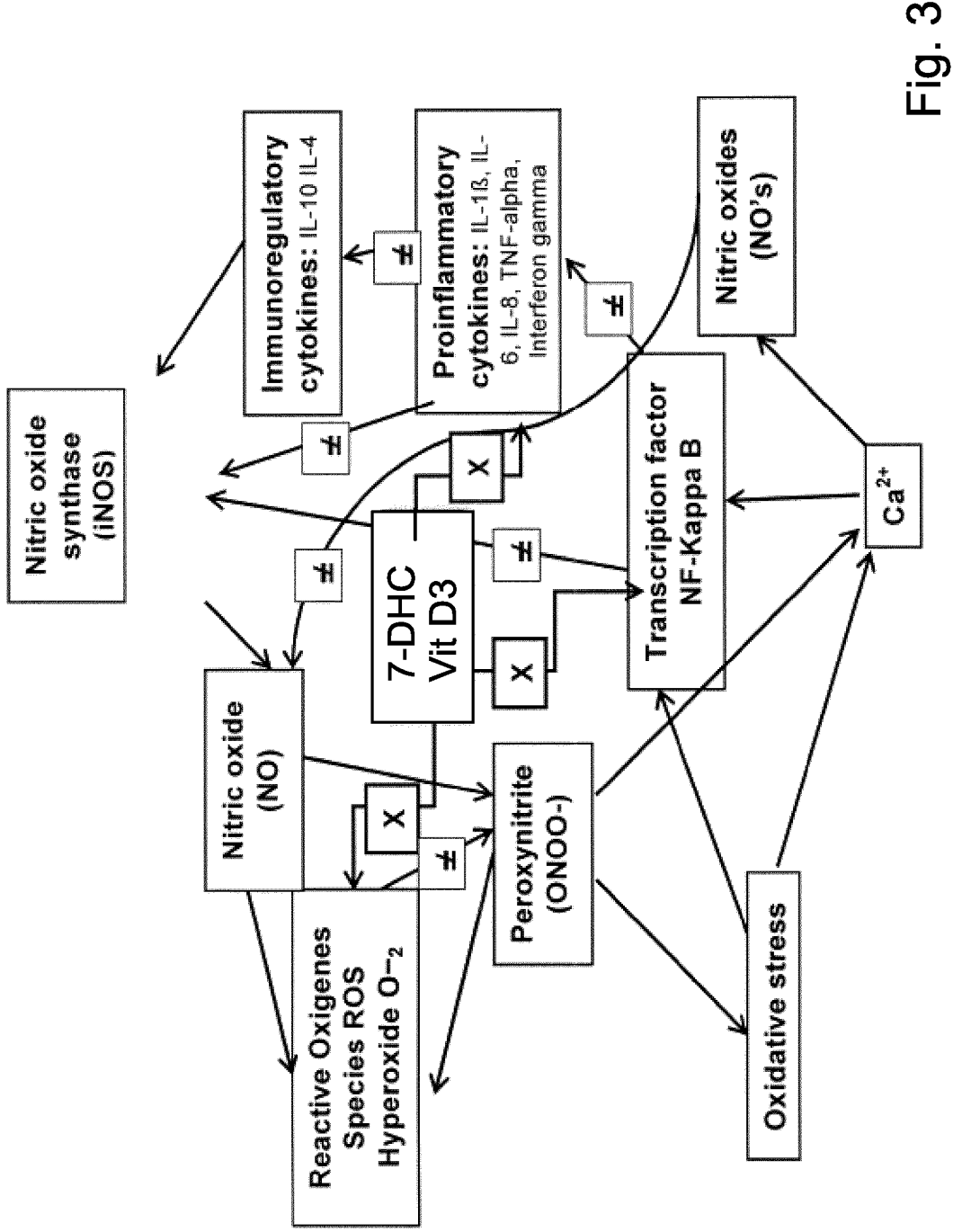
FIG. 3: 7-DHC pathway of potent anti-inflammation activity in the upper layers of the skin after being activated to vitamin D3.

Together with a vitamin D, such as vitamin D3 such as 7-DHC, HA has a synergistic effect on the hydration of the epidermis and also on the immune protective effect [see e.g. 33, 34, 35, 36 FIGS. 2, 3]. HA together with a vitamin D3 such as 7-DHC have a synergistic physico-chemical mode of action on photo damaged skin.

Thus, in a preferred embodiment the composition of the invention comprises 7-DHC in the oil phase of the colloidal carrier system and HA as active substances in the water phase of the colloidal carrier system. The two phases are obtained separately and then combined to form a lipid based colloidal carrier system.

It was further found that 7-DHC also serves as additional activator of the further components (hereinafter also referred to as auxiliary agents), which are particularly effective in the prevention and/or treatment of photodamage. In particular, it was found that compositions further comprising one or more components selected from a vitamin A (preferably retinyl palmitate), at least one vitamin B, a vitamin C (preferably L-ascorbic acid) and a vitamin E (preferably tocopheryl acetate) achieve an effective prevention and/or treatment of photodamage [see FIGS. 1, 2, 3].

Thus in specific embodiments the composition of the invention further comprises one or more, preferably 1, 2, 3, 4, 5, 6, or 7 further components selected from a vitamin A (preferably retinyl palmitate), at least one vitamin B, a vitamin C (preferably L-ascorbic acid) and a vitamin E (preferably tocopheryl acetate).

The term "vitamin A" as used herein refers to retinol, retinal, retinoic acid, and several provitamin A carotenoids (most notably beta-carotene), preferably the major form retinyl palmitate. Vitamin A and particularly retinyl palmitate absorbs light in the short-wavelength UVA range, having a photoprotective effect in the skin. It was found that retinyl palmitate showed an ad on effect together with 7-DHC with regard to absorbing short-wavelength UVA range, the down regulation of NF-κB and therefore on the UV-induced inflammation of the skin [see e.g. 36, 37]. Retinyl palmitate diffuses into the skin, where it is partially hydrolyzed to retinol, penetrates into the stratum corneum, epidermis, and dermis and acts as a UV filter by absorbing UV radiation in the range between 300-350 nm theregy supporting the effects of the compositions of the invention. Typically, retinyl palmitate is used at a concentration of 0.01 wt % up to 2 wt %, preferably 0.01 wt % to 0.5 wt %, more preferably 0.01 to 0.2 wt %, most preferably 0.01 to 0.1 wt %.

The term "vitamin B" as used herein refers a class of water-soluble, chemically distinct vitamins including thiamine (B1), riboflavin (B2), niacin (B3). pantothenic acid (B5), pyridoxine (B36), folate (B7) and various cobalamins (B12). in one embodiment the term "vitamin B" as used herein refers to riboflavin (B2). Typically, riboflavin is used at a concentration of 0.01 wt % to 2 wt %, preferably 0.01 wt % to 0.2 wt %, more preferably 0.01 wt % to 0.1 wt %, most preferably 0.01 wt % to 0.0.05 wt % of the total weight of the composition according to the present invention. In another embodiment, the term "vitamin B" as used herein refers to niacinamide. Niacinamide, an amide of niacin (B3), is a hydrophilic endogenous substance, which has the potential to act as an antioxidant, can improve epidermal barrier function, decrease skin hyperpigmentation, reduce skin atrophy, decrease redness/blotchiness, and improve skin elasticity [54, 55]. Niacinamide shows a synergistic effect with HA in rebuilding the structural and functional integrity of the epidermal barrier function and as humectant of the epidermis [FIG. 2]. Niacinamide controls the NFκB-mediated transcription of signalling molecules by inhibiting the nuclear poly (ADP-ribose) polymerase-1 (PARP-1). Additionally niacinamide will have an added on effect on NFκB-mediated transcription with 7-DHC and vitamin A (particularly retinyl palmitate) [see e.g. 38, 40]. Typically, niacinamide (vitamin B3) is used at a concentration of 0.5 wt % up to 5 wt %, preferably up to 4 wt %, more preferably up to 3 wt %, most preferably 3 wt % of the total weight of the composition according to the present invention.

In another embodiment, the term "vitamin B" as used herein refers to dexpanthenol (provitamin B5). Topical dexpanthenol acts like a humectant and the activity may be based on the hygroscopic properties of dexpanthenol. Dexpanthenol additionally shows protective effects against skin irritation [see e.g. 39. Dexpanthenol significantly accelerates the wound healing process in children post-tonsillectomy intervention [see e.g. 36]. Typically, dexpanthenol (vitamin B5) is used at a concentration of 0.5 wt % up to 5 wt %, preferably of to 3 wt %, more preferably of 2.5 wt %, most preferably 1 wt % of the total weight of the composition according to the present invention.

In a further embodiment the term "vitamin B" as used herein refers to folic acid (B9). Folic acid is essential for DNA synthesis, repair and methylation, in particular nucleotide biosynthesis and remethylation of homocysteine. Folic acid is essential for cellular DNA, RNA production, and is known for its use in the prevention of neural tube defects (NTDs) and serious birth defects and the treatment of anaemia caused by folic acid deficiency. Folic acid also shows in vitro and in vivo in combination with creatine a significant acceleration of the epidermal skin regeneration [see e.g. 41] and thus, can promote a synergistic effect together with 7-DHC covering the UV-induced cell damages and inflammation [FIG. 2]. Typically, folic acid (Vitamin B9) is used at a concentration of 0.01 wt % up to 0.2 wt %, preferably of to 0.07 wt %, more preferably of 0.05 wt %, most preferably 0.02 wt % of the total weight of the composition according to the present invention.

The term "vitamin C" as used herein refers to L-ascorbic acid, which is used as a supplement to treat and prevent scurvy and erythema of the skin [see e.g. 42, 43]. Scurvy leads to the formation of brown spots on the skin, spongy gums, and bleeding from all mucous membranes. L-ascorbic acid acts as an electron donor for different essential enzymes in the skin, which are required for the hydroxylation of proline and lysine in the synthesis of collagen [see e.g. 44, 45, 46 and the synthesis of carnitine, which is essential for the transport of fatty acids into mitochondria for ATP generation in the dermal cells [see e.g. 47, 48]. Ascorbate also acts as an antioxidant, protecting against oxidative stress [see e.g. 49] and is a powerful reducing agent capable of rapidly scavenging a number of reactive oxygen species (ROS) and thus, can promote a synergistic effect together with 7-DHC. Typically, L-ascorbic acid is used at a concentration of 0.1 wt % up to 10 wt %, preferably of to 5 wt %, more preferably of 2 wt %, most preferably 3 wt % of the total weight of the composition according to the present invention.

The term "vitamin E" as used herein refers to compounds known as tocopherols and tocotreienols, preferably tocopheryl acetate. Tocopheryl acetate can penetrate the skin to the living cells, where about 5 wt % is converted to free tocopherol. Tocopheryl acetate has shown antioxidant activities and acts as a peroxyl radical scavenger, disabling the production of damaging free radicals in tissues [see e.g. 50] and thus can promote a synergistic effect together with 7-DHC. Typically, tocopheryl acetate is used at a concentration of 0.1 wt % to 5 wt %, preferably 0.1 wt % to 5 wt %, more preferably 0.1 wt % to 3 wt %, most preferably 0.1 wt % to 2 wt % of the total weight of the composition according to the present invention.

Thus, in preferred embodiments, the composition of the invention comprising 7-DHC and HA further comprises one or more components selected from retinyl palmitate, riboflavin, niacinamide, dexpanthenol, folic acid, L-ascorbic acid and tocopheryl acetate, encapsulated in a lipid based colloidal carrier system. In specific embodiments the composition of the invention comprises 7-DHC and HA as well as a combination of components as follows:

a) Retinyl palmitate and riboflavin or retinyl palmitate and niacinamide or retinyl palmitate and dexpanthenol or retinyl palmitate and folic acid or retinyl palmitate and L-ascorbic acid or retinyl palmitate and tocopheryl acetate.

b) Riboflavin and niacinamide or riboflavin and dexpanthenol or riboflavin and (v) folic acid or riboflavin and L-ascorbic acid or riboflavin and tocopheryl acetate.

c) Niacinamide and dexpanthenol or niacinamide and folic acid or niacinamide and L-ascorbic acid or niacinamide and tocopheryl acetate (vitamin E).

d) Dexpanthenol and folic acid or dexpanthenol and L-ascorbic acid or dexpanthenol and tocopheryl acetate.

e) Folic acid and L-ascorbic acid or folic acid and tocopheryl acetate.

f) L-ascorbic acid and tocopheryl acetate.

Most preferably, the compositions (and topical formulations of the invention comprising 7-DHC and HA further comprise the components retinyl palmitate, riboflavin, niacinamide, dexpanthenol, folic acid, L-ascorbic acid and tocopheryl acetate encapsulated in a lipid based colloidal carrier system. The most preferable concentrations and ranges of concentrations are described as follows in Table 1.

TABLE 1

| Active Ingredients* | Conc. Range wt % | Preferred conc. wt % | CAS-No. |
|---|---|---|---|
| 7-DHC | 0.01-5 | 0.15 | 434-16-2 |
| HA | 0.01-5 | 3 (or 30 mg/ml) | 9004-61-9 |
| Retinyl palmitate | 0.01-0.5 | 0.500 | 79-81-2 |
| Riboflavin | 0.01-0.2 | 0.100 | 83-88-5 |
| Niacinamide | 0.5-4 | 4.000 | 98-92-0 |
| Dexpanthenol | 0.5-2.5 | 2.500 | 81-13-0 |
| Folic acid | 0.01-0.2 | 0.050 | 59-30-3 |
| L-ascorbic acid | 0.1-10 | 3.000 | 50-81-7 |
| Tocopheryl Acetate | 0.1-5 | 2.000 | 7695-91-2 |

*The active ingredients are incorporated in a colloidal carrier system according to the invention (typically: water: >50 wt %, e.g. 50-75 wt %; carrier system 10 wt %; additional oily ingredient, conservants, buffers, filters, 5-25 wt %)

The term "lipid based colloidal carrier (system)" (or "colloid") as used herein refers well known particulate carrier systems, preferably spherical vesicles having at least one lipid bilayer. Typical colloidal carriers include liposomes, niosomes, transferosomes, micelles, nanoparticles, microemulsions and others, preferably liposomes, niosomes, transferosomes, most preferably liposomes. Depending on their size and number of bilayers, the lipid based colloidal carrier systemis in form of: (a) multilamellar vesicles (MLV), (b) large unilamellar vesicles (LUV), (c) small unilamellar vesicles (SUV), (d) multivesicle vesicles (MW), oligolamellar vesicles (OLV). The preferred particle size ranges from 10-500 nm, preferably 10 to 300 nm, more preferably 20-150 nm.

In specific embodiments, the colloids are based on natural and/or synthetic phospholipids and compose typically 10 wt % of the formulation. Typically used phospholipids include fatty acids having a phosphate-containing polar endgroup which is hydrophilic and thus soluble in water, and a hydrophobic end group, which is soluble in fats joined together by a glycerol molecule (e.g. glycerophospholipids) or sphingosine molecule (e.g. phosphosphingolipids).

In some embodiments, the phospholipids used in the colloidal carrier system include one or more of phosphatidylcholine, lysophosphotidylcholine, hydrogenated phospholipids, and unsaturated phospholipids. Examples of glycerophospholipids include phosphatidic acid (phosphatidate) (PA), phosphatidylethanolamine (cephalin) (PE), phosphatidylcholine (lecithin) (PC), Phosphatidylserine (PS), and Phosphoinositides, which further include phosphatidylinositol (PI), phosphatidylinositol phosphate (PIP), phosphatidylinositol bisphosphate (PIP2), and phosphatidylinositol triphosphate (PIP3). Examples of phosphosphingolipids include ceramide phosphorylcholine (sphingomyelin) (SPH), ceramide phosphorylethanolamine (sphingomyelin) (Cer-PE), and ceramide phosphorylglycerol. The colloidal carrier system of the invention may further comprise fatty acids such as omega-3, omega-6 and omega-9 fatty acids. Preferred examples used in the present invention are lecithin, sphingomyeline, phosphatidylcholine, linoleic acid, linolenic acid, caprylic acid, capric acid, Lupinus albus seed oil, Squalene, Imidazolidinyl Urea and Sodium Ascorbyl Phosphate. A preferred embodiment of a lipid based colloidal carrier system is shown in Table 2.

TABLE 2

| Ingredients (INCI) | Conc. range wt % | Quantity wt % | CAS-No. |
|---|---|---|---|
| Phosphatylcholine | 0-2-80 | 40.00 | 8002-43-5 |
| Sphingomyeline | 0-2-80 | 20.00 | 85187-10-6 |
| Linolenic Acid | 0-5-50 | 10.00 | 463-40-1 |
| Linoleic Acid | 0-5-50 | 10.00 | 60-33-3 |
| Caprylic Triglyceride | 0.2-40 | 10.00 | 73398-61-5 |
| Capric Triglyceride | 0.2-40 | 10.00 | 65381-09-1 |
| Total: | | 100.00 | |

In a further embodiment, the colloidal carrier system can also include a polycarbonate, a Polyvinylpyrrolidon (PVP), also Polyvidon or Povidonmembranes, preferably copovidone of a MW 10 nm-500 nm. Copovidone will be used as film-forming agent and binder and also as carrier system.

For use in the present invention, the lipophilic agents will be encapsulated within the bilayer system, whereas the hydrophilic agents will be encapsulated in the aqueous phase of the system. Thus, the vitamin D precursor (such as 7-DHC or a derivative thereof) and the phospholipid(s) and optional additional lipophilic agents (e.g. retinyl palmitate and tocopheryl acetate) are directly incorporated in the oil phase of the colloidal carrier system at room temperature. In a separate step, the HA and optional additional hydrophilic agents (e.g. riboflavin, niacinamide, dexpanthenol, folic acid, L-ascorbic acid) are mixed together separately in an aqueous solution. The aqueous solution comprising HA and optional additional hydrophilic agents are mixed to the oil phase comprising the vitamin D precursor (such as 7-DHC or a derivative thereof). After emulsification of the two phases, the hydrophilic components (HA and additional hydrophilic agents) of the compositions are present in aqueous compartments while the lipophilic components of the compositions already insert themselves with the first step in phospholipid bilayers of the particles.

Thus, in most preferred embodiments, the lipid based colloidal carrier system (preferably lipid based vesicles such as liposomes, niosomes, tranferosomes) is composed of lecithin, linolenic acid, linoleic acid, phosphatidylcholin and paprylic/papric triglyceride, which is charged with the components Vitamin D3, such as 7-DHC or a derivative thereof, and HA and optionally at least one, preferably 1, 2, 3, 4, 5, 6 or 7 of the components retinyl palmitate, riboflavin, niacinamide, dexpanthenol, folic acid, L-ascorbic acid and tocopheryl acetate. The uniquely charged and stable carrier system will allow penetrating the skin in the upper layers of the skin to allow the synergistic compositions of the invention to take effect directly at the desired site.

Depending on the nature and type of application, the compositions of the invention may further comprise one or more pharmaceutically acceptable additives, excipients, adjuvants commonly used in formulations used for application to the skin and/or mucous membranes.

Typical additives include e.g. a relevant UV filter system or one or more UVA/B protectants for prevention of photodamage and sun UVA and UVB protection such as Fillagrine trans-Urocanin Acide, Butyl Methoxydibenzoylmethane Neo Heliopan 357 Eusolex 9020, Parsol 1789, Methylene Bis-Benzotriazolyl Tetramethylbutylphenol (nano), Tinosorb M, Ethylhexyl Triazone Uvinul T 150, Bis-Ethylhexyloxyphenol Methoxyphenyl Triazine Tinosorb S, Ethylhexyl Methoxycinnamate Uvinul MC 80, Parsol MCX, Neo Heliopan AV 4, and the like. The UV filter(s) are embedded with the active ingredients and auxiliary ingredients for the prevention of skin erythema and actinic keratosis, or other forms of non melanoma skin cancer (NMSC).

Typical adjuvants include e.g. surfactants, emulsifying agents, emollients, thickening agents, conditioning conservants, buffering agents, humectants, perfuming agents, and the like. Thus, the carrier system may further comprise one or more surfactants. The term "surfactant" refers to a material which lowers the surface tension of a liquid and the interfacial tension between two liquids, allowing their easier spreading. Surfactants have a hydrophilic head that is attracted to water molecules and a hydrophobic tail that repels water and simultaneously attaches itself to oil and grease in dirt. These opposing forces loosen the dirt and suspend it in the water, having the ability to remove it from surfaces such as the human skin, textiles, and other solids, when surfactants are dissolved in water. Examples of appropriate surfactant agents include, but are not limited to, non-ionic, ionic (either anionic or cationic) or zwitterionic (or amphoteric wherein the head of the surfactant contains two oppositely charged groups) surfactants. Examples of anionic surfactants include, but are not limited to, those based on sulfate, sulfonate or carboxylate anions such as perfluorooctanoate (PFOA or PFO), alkyl benzene sulfonate, soaps, fatty acid salts, or alkyl sulfate salts such as perfluorooctanesulfonate (PFOS), sodium dodecyl sulfate (SDS), ammonium lauryl sulfate, or sodium lauryl ether sulfate (SLES). Examples of cationic surfactants include, but are not limited to, those based on quaternary ammonium cations such as or alkyltrimethylammonium including cetyl trimethylammonium bromide (CTAB) a.k.a., or hexadecyl trimethyl ammonium bromide, cetylpyridinium chloride (CPC), polyethoxylated tallow amine (POEA), benzalkonium chloride (BAC), or benzethonium chloride (BZT). Examples of zwitterionic surfactants include, but are not limited to dodecyl betaine, cocamidopropyl betaine, or coco ampho glycinate. Examples of non-ionic surfactants include, but are not limited to, alkyl poly(ethylene oxide), alkylphenol poly(ethylene oxide), copolymers of poly(ethylene oxide), poly(propylene oxide) (commercially called Poloxamers or Poloxamines), alkyl polyglucosides including octyl glucoside and decyl maltoside, fatty alcohols including cetyl alcohol and oleyl alcohol, cocamide MEA, cocamide DEA, or polysorbates including tween 20, tween 80, or dodecyl dimethylamine oxide. Preferably, the surfactant is foaming and skin friendly, including polysorbates, such as polysorbate 20 or 40, coco glucoside, lauryl glucoside, decyl glucoside, lauryl sulfates such as ammonium, sodium, magnesium, MEA, triethylamine (TEA), or mipa lauryl sulfate, cocamidopropyl betain, or sodium alkyl sulfosuccinates.

In specifc embodiments the surfactant is at least one polysorbate, e.g. polysorbate 10-150, which are non-ionic surfactants commonly used as excipients and emulsifiers. Preferably the polysorbate is a polysorbate-type nonionic surfactant formed by the ethoxylation of sorbitan before the addition of lauric acid as Scattics, PS20 as Alkest TW 20 and Tween 20. Polysorbates have efficiency in the stabilization of the colloidal carrier and in the presence of liquid lipids with different fatty acid C-chains produces with less organized crystalline structure can provides better loading capacity for active substance accommodation. The effect of polysorbate will be in the stabilization the carrier system through the physiochemical properties of the formulated nanoparticles. The colloidal carrier system are stabilized with polysorbate like polysorbate 20 or polysorbate 80. Polysorbate will be used as better dispersing agent for the liposomal carrier system. The small size and superior particle surface to volume ratio would increase loading efficiency and bioavailability of the active substance, thus making the liposomal carrier system a more efficient delivery system.

In other specific embodiments the surfactant is polyvinylpyrrolidone (PVP), which is known to either prevent precipitation or reduce the size of the resulting particles of the active ingredients or auxiliary substances with strongly pH-dependent aqueous solubility. The PVP like poloxamer/copovidone will be used to stabilize particles in the liposomal formulation. It is presumed, that the dissolution efficiency is higher with Polyvinylpyrrolidone (PVP) and is increased with increased polymer concentration. PVP is typically used as stabilisation and to increase efficiency and bioavailability of the liposomal carrier system.

Thus, in specific embodiments the carrier system may further compromise a polycarbonate, Polyvinylpyrrolidon (PVP), Polyvidon, Povidonmembranes, Povidone, Copovidone, Hypromellose and Eudragit EPO, preferably Copovidone of a MW 10 nm-500 nm.

The amount of the surfactant in the compositions of the present invention is between 0.5 and 10 wt % of the total weight of the composition according to the present invention.

The term "emollient" agent refers to an agent that softens and soothes the skin in order to correct dryness and scaling of the skin, lubricating the skin surface, encouraging skin water retention, and altering product textures. Examples of appropriate topical emollient agents include, but are not limited to, octyl hydroxystearate, lanolin, caprylic/capric triglyceride, cetyl palmitate, octyldodecanol, cetyl alcohol, isopropyl isostearate, glyceryl dilaurate, isopropyl myristate, palm alcohol, dimethicone, squalane, plukenetia volubilis seed oil, butyrospermum parkii butter, sucrose cocoate, or their mixtures. Preferably the emollient is selected from the group consisting of dimethicone, squalane, plukenetia volubilis seed oil, butyrospermum parkii butter, caprylic/capric triglyceride, octyldodecanol, or their mixtures. The amount of emollient agent in the compositions of the present invention is between 10 and 30 wt % of the total weight of the composition according to the present invention.

The term "humectant" agent refers to a hygroscopic agent which attracts water molecules from the surrounding environment though either absorption or adsorption, preventing the skin from losing moisture. Examples of appropriate topical humectants include, but are not limited to, glycerin, diglycerin, ethylhexylglycerin, glucose, honey, lactic acid, polyethylene glycol, propylene glycol, sorbitol, sucrose, or threalose. Preferably, the humectant is selected group consisting of glycerin, diglycerin, ethylhexylglycerin, and their mixtures. The amount of the humectants in the compositions of the present invention is between 0.5-15 wt %, preferably 0.5-10 wt %, of the total weight of the composition according to the present invention.

The term "thickening agent" or "thickener" or "viscosity agent" which is herein used interchangeably refers to a material that increases its viscosity without substantially modifying its other properties. Examples of appropriate viscosity agents include, but are not limited to, cellulose or their derivatives such as hydroxypropyl methylcellulose, polyethylene glycol, microcrystalline cellulose, cetearyl alcohol, alginates, branched polysaccharides, fumed silica, xanthan gum, carbomer, and polyacrylates. Preferably, the viscosity agent is selected group consisting of microcrystalline cellulose, cetearyl alcohol, cellulose, xanthan gum, and carbomer. The amount of the viscosity agents in the compositions of the present invention is between 0.5 and 15 wt %, preferably 0.5-10 wt %, of the total weight of the composition according to the present invention.

The term "emulsifying agent" or "emulsifier" which is herein used interchangeably refers to a material that reduces surface tension, promoting the formation of intimate mixtures of non-miscible liquids by altering the interfacial tension. Emulsifier stabilizes an emulsion by increasing its kinetic stability. Examples of appropriate emulsifier include, but are not limited to, glyceryl trioleate, glyceryl oleate, acetylated sucrose distearate, sorbitan trioleate, polyoxyethylene monostearate, glycerol monooleate, sucrose distearate, polyethylene glycol monostearate, octyl phenoxypoly(ethyleneoxy) ethanol, deacylerin penta-isostearate, sorbitan sesquioleate, hydroxylated lanolin, lecithin, lanolin, triglyceryl diisostearate, polyoxyethylene oleyl ether, calcium stearoyl-2-lactylate, sodium lauroyl lactylate, sodium stearoyl lactylate, cetearyl glucoside, methyl glucoside sesquistearate, sorbitan monopalmitate, methoxy polyethylene glycol-22/dodecyl glycol copolymer, polyethylene glycol-45/dodecyl glycol copolymer, polyethylene glycol 400 distearate and glyceryl stearate, candelilla/jojoba/rice bran polyglyceryl-3 esters, cetyl phosphate, potassium cetyl phosphate, or their mixtures. Preferably, the emulsifier is selected group consisting of glyceryl oleate, lecithin, sodium lauroyl lactylate, sodium stearoyl lactylate, glyceryl stearate, candelilla/jojoba/rice bran polyglyceryl-3 esters, and their mixtures. The amount of the emulsifier in the compositions of the present invention is between 0.5 and 15 wt %, preferably 0.5-10 wt %, of the total weight of the composition according to the present invention.

The term "pH-regulating" or "buffering" agent refers to acids or bases that can be used to adjust the pH of the finished product to the desired level, without affecting the stability of the solution. Examples of appropriate topical pH-regulating agents include, but are not limited to, acetic acid, lactic acid, citric acid, gluconic acid, ethanolamine, formic acid, oxalic acid, tartaric acid, potassium hydroxide, sodium hydroxide, triethanolamine, or their mixtures. Preferably, the pH-regulating agent is selected group consisting of triethanolamine, sodium hydroxide, lactic acid, and citric acid. The amount of the pH-regulating agent in the compositions of the present invention is between 0.01 and 1 wt % of the total weight of the composition according to the present invention.

The term "conditioning conservant" refers to a compound that has a moisturizing function, more specifically a compound that acts on the barrier function, for the purpose of keeping the stratum corneum moisturized, such as ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes, petroleum jelly and lanolin; or a compound which directly increases the water content of the stratum corneum, such as threalose and its derivatives, glycerol, pentanediol, pidolates, serine, xylitol, peroxyethanol, sodium lactate, glyceryl polyacrylate, ectoin and its derivatives, chitosan, oligo- and polysaccharides, cyclic carbonates, N-lauroylpyrrolidonecarboxylic acid and N-α-benzoyl-L-arginine. The amount of duch compounds in the composition of the present invention is from 0.001 wt % to 30 wt %, preferably from 0.01 to 20 wt %, of the total weight of the composition according to the present invention.

The term "perfuming agent" refers to any perfume or aroma which is capable of releasing an agreeable odor. The perfuming substance contained in the compositions of the invention may derive from perfumes and aromas of natural or synthetic origin and mixtures thereof. Examples of perfumes and aromas of natural origin are flower extracts (lily, lavender, rose, jasmine, ylang-ylang), stems and leaves (patchouli, geranium, bitter leaf), fruits (coriander, anis, cumin, juniper), fruit skin (bergamot, lemon, orange), roots (angelica, celery, cardamom, iris, sweet flag), wood (pinewood, sandalwood, lignum vitae, pink cedar), herbs and graminaceae (tarragon, lemon grass, sage, thyme), needles and branches (spruce, fir, pine, dwarf pine), resins and balsams (galbanum, gum elemi, gum benzoin, myrrh, frankincense, opopanax).

Preferably, the quantity of perfuming agents is from 1 wt % to 30 wt % by weight, more preferably 2 wt % to 25 wt % by weight with respect to the total composition weight. A preferred composition is shown in Table 3.

TABLE 3

| Ingredients (INCI) without active substances and phospholipides of the carrier system | Quantity wt % | Function | CAS-No. |
| --- | --- | --- | --- |
| Aqua destillata | 56.79 | Solvent | 7732-18-5 |
| Isopropyl Myristate | 1.0 | Emulsifying Emolient | 110-27-0 |
| Palmitoyl Tripeptide-5 | 1.0 | Emulsifying Emolient | 623172-56-5 95 |
| Palmitic Acid | 1.0 | Emulsifying Emolient | 57-10-3 |
| Glycerin | 3.0 | Emulsifying Emolient | 56-81-5 |
| Lupinus albus seed oil | 2.0 | Emulsifying Emolient | 545-47-1 |
| Palmitoyl-Pentapeptid | 1.0 | Emulsifying Emolient | 214047-00-4 |
| Cetearyl Alcohol | 1.0 | Emulsifying Emolient | 67762-27-0/ 8005-44-5 |
| Polidocanol | 3.0 | Emulsifying Emolient | 3055-99-0 |
| Squalene | 1.0 | Emulsifying Emolient | 111-02-4 |
| Hydroxypalmitoyl Sphinganine | 1.0 | Emulsifying Emolient | 190249-36-6 |
| Imidazolidinyl Urea | 2.0 | Humectant | 39236-46-9 |
| Prunus amygalus dulcis oil | 5.0 | Conditioning Conservant | 8007-69-0/ 90320-37-9 |
| Pyridoxine hydrochloride | 1.0 | Conditioning Conservant | 58-56-0 |
| Sodium Ascorbyl Phosphate | 2.0 | Conditioning Conservant | 66170-10-3 |
| Phenoxyethanol/ Peroxyethanol | 1.0 | Conditioning Conservant | 122-99-6 |

TABLE 3-continued

| Ingredients (INCI) without active substances and phospholipides of the carrier system | Quantity wt % | Function | CAS-No. |
|---|---|---|---|
| Green Tea Polyphenole | 1.0 | Conditioning Conservant | 84650-60-2 |
| Sodium Citrate | 1.0 | Buffering | 68-04-2 |
| PEG-5 Glyceryl Stearate | 1.0 | Surfactant | 51158-08-8 138860-92-1 |
| Stearic Acid | 1.0 | Surfactant | 57-11-44 |
| Fillagrine trans-Urocanin Acide | 1.0 | UV-fdter | 104-98-3- 3465-72-3 |
| Butyl Methoxydibenzoylmethane | 4.8 | UV Filter | 70356-09-1 |
| Methylene Bis- Benzotriazolyl Tetramethylbutylphenol (nano) | 3.5 | UV Filter | 103597-45-1 |
| Ethylhexyl Triazone | 2.0 | UV Filter | 88122-99-0 |
| Bis-Ethylhexyloxyphenol Methoxyphenyl Triazine | 0.8 | UV Filter | 187393-00-6 |
| Ethylhexyl Methoxycinnamate | 0.1 | UV Filter | 5466-77-3 |
| Octyl dodecanol | 1.0 | Perfuming | 5333-42-6 |
| Geranium Maculatum Oil | 0.002 | Perfuming | 84650-10-2 |
| Citrus Aurantium Dulcis Oil | 0.002 | Perfuming | 8008-57-9 |
| Citrus Medica Limonum Peel Oil | 0.002 | Perfuming | 8008-56-8/ 84929-31-7 |
| Aniba Rosaeodora Oil | 0.004 | Perfuming | 83863-32-5 |
| Total: | 100.00 | | |

Lipid based colloidal carrier system (e.g. lipid based vesicles such as liposomes, niosomes, tranferosomes) can be prepared by any of the techniques known (for the preparation of lipid based carrier systems in general, see e.g. Liposomes, eds. Angel Catala, pub. InTech, 2017 (ISBN 978-953-51-3580-7), or of liposomal carriers see e.g. Liposomes, Methods and Protocols, Springer Protocols, eds. D'Souza, Gerard G. M., 2017). For example, the colloid can be formed by any conventional technique for preparing multilamellar lipid vesicles (MLVs), that is, by placing the lipophilic vitamin D3 or precursor thereof with one or more lipids in a suitable vessel, dissolving the lipids in an organic solvent, e.g. chloroform, and evaporating the organic solvent to obtain a lipid film. In a subsequent step hydration of the lipid film is achieved by adding an aqueous solution containing the hydrophilic components including the hyaluronic acid. Typically the obtained lipid suspension is subjected to swirling or vortexing to give the final composition according to the invention. Alternatively, techniques used for producing large unilamellar lipid vesicles (LUVs), such as reverse-phase evaporation, infusion procedures, and detergent dilution, can be used to produce the liposomes. A review of these and other methods for producing lipid vesicles can be found in the text Liposome Technology, Volume I, Gregory Gregoriadis Ed., CRC Press, Boca Raton, Fla., (1984), which is incorporated herein by reference. For example, the lipid-containing particles can be in the form of steroidal lipid vesicles, stable plurilamellar lipid vesicles (SPLVs), monophasic vesicles (MPVs), or lipid matrix carriers (LMCs). In the case of MLVs, if desired, the liposomes can be subjected to multiple (five or more) freeze-thaw cycles to enhance their trapped volumes and trapping efficiencies and to provide a more uniform interlamellar distribution of solute.

In one embodiment, the liposomes are for example prepared by hot high pressure homogenization to reach high encapsulation efficiency (EE). The encapsulation efficiency will give the percentage of active substance that is successfully entrapped/adsorbed into nanoparticles and will be carried into the depper layers of the skin. A major obstacle to the application of nanostructured lipid carriers (NLCs) as carriers for hydrophilic active substances is the limited loading capacity (LC) and encapsulation efficiency (EE) of NLCs for these molecules, with wt % EE being equal to the [(active substance added−Free "unentrapped active substance")/active substance added]*100 (thus as an example, an wt % EE of 5 wt % means that 5 wt % of the active substance is entrapped into the carrier system).

The phase transfer temperature from the gel form to the crystalline two dimensional grid states with less mobility in a fluid crystalline structure. The phase transfer temperature of the mentioned lipids is depending of the head group, chain lengths and the saturation level esters of fatty acids. The temperature will be from −20° C. to 60° C. and can be established with the thermoanalytic methods. Embedded in the fluid crystalline phase the mobility of the lipophilic agents increases and can exchange the place within the lipid layers, but not abandon the lipid layers [46].

The physical structure of the multilamellar layer system will be created throughout interactions between the phospholipids and the aqueous medium with the high pressure homogenisation and dehydration of dry lipids. With this method multilamellar vessels (MLV) are built. The polycarbonate membranes of a size 10-500 nm will be used for the liposomes extrusion. The homogenisation and size will be determined throughout the pore diameter of the filter and the number of the extrusion steps. Aim will be to reach the highest encapsulation efficiency.

The use of this carrier system has unique physicochemical properties, such as ultra-small size (small particles from 1-100 nm dimension range), large surface area to mass ratio, and high reactivity, which are different from bulk materials of the same composition. These properties are being used to overcome the limitation of skin penetration with larger size of molecules and encapsulate as needed lipophilic and hydrophilic substances to pass the skin barrier.

In a further aspect the invention is directed towards suitable formulations of the compositions of the invention for topical or transdermal application.

The compositions of this invention can be used in different types of topical or transdermal applications, which may be in solid, liquid or semisolid form. Thus, suitable formulations include, but are not limited to, emulsions (e.g. oil and/or silicone in water emulsions, water-in-oil and/or silicone emulsions, water/oil/water or water/silicone/water type emulsions, and oil/water/oil or silicone/water/silicone type emulsions), microemulsions, aqueous dispersions, oils, milks, balsams, foams, aqueous or oily lotions, aqueous or oily gels, creams, solutions, hydroalcoholic solutions, hydroglycolic solutions, hydrogels, serums, ointments, mousses, pastes, sprays or aerosols, as well as inclusion of the compositions of the invention in any transdermal patches. In a typical transdermal therapeutic system, such as a patch or pad, the compositions of the invention (with or without at least one auxiliary agent) are embedded, if desired, in combination with penetration reinforcing agents and/or crystallisation inhibitors. Thus, in specific embodiments the compositions are in form of a cream or a gel or a lotion, in other specific embodiments the compositions are in form of transdermal therapeutic system, such as a patch or pad.

In a further aspect, the invention is directed towards the use of the composition (and formulations thereof) of the invention in the prevention and/or treatment of skin photo damage symptoms, in particular in the prevention and/or treatment of skin atrophy, skin dyspigmentation (patches/spots), photodermatitis (erythema: skin inflammation and redness), telangiectasia, (couperose) and prevention of actinic keratosis, as well to protect the skin from the sun, UVA and UVB radiation.

Thus, the present invention contemplates a method of prevention and/or treatment of photodamage of the skin of a subject comprising administering a composition (and topical formulations thereof) of the invention to the subject in an amount effective to stop the photodamage process, i.e. to inhibit reactive oxygen species ROS, hyperoxide O-2 and nitric oxide (NO), and therefore accumulation of cytotoxic peroxynitrite (ONOO—).

The compositions (or formulations thereof) may be either administered at regular intervals as needed (e.g., once, twice or several times a day) or in an essentially continuous manner (e.g. via a transdermal patch).

The following examples are representative examples to illustrate the invention, without limiting the scope of the invention.

EXAMPLES

Methods and Materials

Dried phospholipides were dispersed at room temperature in aqueous solution forming spontaneously spheric colloids. 7-DHC of purity 98.7% (hplc; area %) was liquefied at temperatures between 140 and 150° C. Propylenglycol was added to the liquefied 7-DHC and the obtained mixture was admixed to the phospholipids colloids under vigorous stirring at room temperature to obtain colloid forming spheres of 20-150 nm adding 7-DHC in the oil phase of the colloids. HA (2% low molecular 4 KDa 96.8% of purity, 0.5 wt % of medium molecular 48.3 KDa 97.3% purity and 0.5 wt % of high molecular $1.78 \times 10^6$ Da eye drop grade of purity 100%) was dispersed/dissolved under stirring in water and added under stirring at room temperature separately. HA mixtures were added to the phospholipids colloids already charged with 7-DHC and stirred for 20 minutes at room temperature to obtain spontaneous formation of a homogeneous hydrogel. The microscopic analysis showed spheric particles of 20-150 nm size. The hydrogel was macroscopic and according to HPLC analysis stable showing the same concentration of added 7-DHC over 6 months.

For the lipid phase 7-DHC of purity 98.7% (hplc; area %) was used (liquefied at temperatures between 140 and 150° C.). Propylenglycol was used as the organic solvent for the 7-DHGC and the phospholipids.

HA (in form of a mixture of 2% low molecular 4 KDa 96.8% of purity, 0.5 wt % of medium molecular 48.3 KDa 97.3% purity and 0.5 wt % of high molecular $1.78 \times 10^6$ Da eye drop grade of purity 100%) was used for the aqueous phase.

Stirring for 20 minutes at room temperature resulted in a spontaneous formation of a homogeneous hydrogel. The microscopic analysis showed spheric particles of 20-150 nm size.

Stability studies showed high stability (≥98%) for 6 months and constant content of 1.5% of DHC in the analytic (HPLC).

Example 1 without UV-Filter System Cream

TABLE 4

| Ingredients (INCI) | Quantity wt % | CAS-No. | |
|---|---|---|---|
| 7-DHC | 0.15 | 434-16-2 | |
| HA | 3 | 9004-61-9 | |
| Retinyl Palmitate | 0.5 | 79-81-2 | Skin Conditioning |
| Riboflavin | 0.1 | 83-88-5 | |
| Niacinamide | 4.0 | 98-92-0 | |
| Dexpanthenol | 2.5 | 81-13-0 | |
| Folic acid | 0.05 | 59-30-3 | |
| L-ascorbic acid | 3.0 | 50-81-7 | |
| Tocopheryl Acetate | 2.0 | 7695-91-2 | |
| Aqua destillata | 46.196 | 7732-18-5 | Solvent |
| PEG-5 Glyceryl Stearate | 1.0 | 51158-08-8 138860-92-1 | Surfactant |
| Stearic Acid Emulsifying Emolient | 1.0 | 57-11-44 | |
| Isopropyl Myristate | 1.0 | 110-27-0 | |
| Palmitic Acid | 1.0 | 57-10-3 | |
| Lupinus albus Ölextrakt | 2.0 | 545-47-1 | |
| Palmitoyl-Pentapeptid | 1.0 | 214047-00-4 | |
| Prunus amygalus dulcis oil | 5.0 | 8007-69-0/ 90320-37-9 | |
| Squalene | 1.0 | 111-02-4 | |
| Polidocanol | 3.0 | 3055-99-0 | |
| Hydroxypalmitoylsphinganin | 1.0 | 190249-36-6 | |
| Pyridoxine HCL | 5.0 | 8007-69-0/ 90320-37-9 | Conditioning Conservant |
| Sodium Ascorbyl Phosphate | 2.0 | 66170-10-3 | |
| Sodium Citrate | 1.0 | 6132-04-3 | Buffer |
| Lecithin | 2 | 8002-43-5 | Carrier encapsulation formulary* |
| Sphingomyeline | 2 | 85187-10-6 | |
| Linolenic Acid | 1 | 463-40-1 | |
| Linoleic Acid | 1 | 60-33-3 | |
| Phosphatidylcholin | 3 | 26853-31-6 | |
| Caprylic Triglyceride | 1 | 73398-61-5 | |
| Octyl dodecanol | 1.0 | 5333-42-6 | Perfume |
| Citrus Aurantium Dulcis Oil | 0.002 | 8008-57-9 | |
| Citrus Medica Limonum Peel Oil | 0.002 | 8008-56-8/ 84929-31-7 | |
| VP/Eicosene Copolymer | 2.5 | 28211-18-9 | Film Former |
| Total: | 100 | | |

Example 2 without UV-Filter System Gel

TABLE 5

| Ingredients (INCI) | Quantity wt % | Function | CAS-No. |
|---|---|---|---|
| 7-DHC | 0.15 | Active ingredient ROS binder | 434-16-2 |
| HA | 3 | Active ingredient Humectant | 9004-61-9 |
| Retinyl Palmitate | 0.5 | Skin Conditioning | 79-81-2 |
| Riboflavin | 0.1 | Skin Conditioning | 83-88-5 |
| Niacinamide | 4.0 | Skin Conditioning | 98-92-0 |
| Dexpanthenol | 2.5 | Skin Conditioning | 81-13-0 |
| Folic acid | 0.05 | Skin Conditioning | 59-30-3 |
| L-ascorbic acid | 3.0 | Skin Conditioning | 50-81-7 |
| Tocopheryl Acetate | 2.0 | Skin Conditioning | 7695-91-2 |

TABLE 5-continued

| Ingredients (INCI) | Quantity wt % | Function | CAS-No. |
|---|---|---|---|
| Aqua destillata | 65.77 | Solvent | 7732-18-5 |
| Stearic Acid | 1.0 | Surfactant | 57-11-44 |
| Isopropyl Myristate | 1.0 | Emulsifying Emolient | 110-27-0 |
| Palmitic Acid | 1.0 | Emulsifying Emolient | 57-10-3 |
| Cetearyl Alcohol | 1.0 | Emulsifying Emolient | 67762-27-0/ 8005-44-5 |
| Polidocanol | 2.0 | Emulsifying Emolient | 3055-99-0 |
| Sodium Citrate | 1.0 | Buffering | 6132-04-3 |
| Lecithin | 1 | Carrier encapsulation formulary* | 8002-43-5 |
| Sphingomyeline | 2 | Carrier encapsulation formulary* | 85187-10-6 |
| Linolenic Acid | 1 | Carrier encapsulation formulary* | 463-40-1 |
| Linoleic Acid | 1 | Carrier encapsulation formulary* | 60-33-3 |
| Phosphatidylcholin | 2.0 | Carrier encapsulation formulary* | 26853-31-6 |
| Caprylic Triglyceride | 1 | Carrier encapsulation formulary* | 73398-61-5 |
| Capric Triglyceride | 1 | Carrier encapsulation formulary* | 65381-09-1 |
| Triethanolamine | 0.08 | ph-adjusting | 102-71-6 |
| Peroxyethanol | 3 | Conservant | 95684-29-0 |
| Total: | 100 | | |

Example 3 without UV-Filter System Serum

TABLE 6

| Ingredients (INCI) | Quantity wt % | Function | CAS-No. |
|---|---|---|---|
| 7-DHC | 0.15 | Active ingredient ROS binder | 434-16-2 |
| HA | 3 | Active ingredient Humectant | 9004-61-9 |
| Dexpanthenol | 2.5 | Skin Conditioning | 81-13-0 |
| Folic acid | 0.05 | Skin Conditioning | 59-30-3 |
| Tocopheryl Acetate | 2.0 | Skin Conditioning | 7695-91-2 |
| Aqua destillata | 70.3 | Solvent | 7732-18-5 |
| PEG-5 Glyceryl Stearate | 1.0 | Surfactant | 51158-08-8 138860-92-1 |
| Stearic Acid | 1.0 | Surfactant | 57-11-44 |
| Isopropyl Myristate | 1.0 | Emulsifying Emolient | 110-27-0 |
| Palmitic Acid | 1.0 | Emulsifying Emolient | 57-10-3 |
| Palmitoyl-Pentapeptid | 1.0 | Emulsifying Emolient | 214047-00-4 |
| Polidocanol | 2.0 | Emulsifying Emolient | 3055-99-0 |
| Hydroxypalmitoylsphinganin | 1.0 | Emulsifying Emolient | 190249-36-6 |
| Sodium Citrate | 1.0 | Buffering | 6132-04-3 |
| Lecithin | 1 | Carrier encapsulation formulary* | 8002-43-5 |
| Sphingomyeline | 2 | Carrier encapsulation formulary* | 85187-10-6 |
| Linolenic Acid | 1 | Carrier encapsulation formulary* | 463-40-1 |

TABLE 6-continued

| Ingredients (INCI) | Quantity wt % | Function | CAS-No. |
|---|---|---|---|
| Linoleic Acid | 1 | Carrier encapsulation formulary* | 60-33-3 |
| Phosphatidylcholin | 3 | Carrier encapsulation formulary* | 26853-31-6 |
| Caprylic Triglyceride | 1 | Carrier encapsulation formulary* | 73398-61-5 |
| Capric Triglyceride | 1 | Carrier encapsulation formulary* | 65381-09-1 |
| Peroxyethanol | 3 | Conservant | 95684-29-0 |
| Total: | 100 | | |

Example 4 with UV-Filter System Face

TABLE 7

| Ingredients (INCI) | Quantity wt % | Function | CAS-No. |
|---|---|---|---|
| 7-DHC | 0.15 | Active ingredient ROS binder | 434-16-2 |
| HA | 3 | Active ingredient Humectant | 9004-61-9 |
| Aqua destillata | 55.15 | Solvent | 7732-18-5 |
| PEG-5 Glyceryl Stearate | 1.0 | Surfactant | 51158-08-8 138860-92-1 |
| Stearic Acid | 1.0 | Surfactant | 57-11-44 |
| Isopropyl Myristate | 1.0 | Emulsifying Emolient | 110-27-0 |
| Palmitic Acid | 1.0 | Emulsifying Emolient | 57-10-3 |
| Pyridoxine HCL | 5.0 | Conditioning Conservant | 8007-69-0/ 90320-37-9 |
| Sodium Ascorbyl Phosphate | 2.0 | Conditioning Conservant | 66170-10-3 |
| Polidocanol | 3.0 | Emulsifying Emolient | 3055-99-0 |
| Hydroxy-palmitoylsphinganin | 1.0 | Emulsifying Emolient | 190249-36-6 |
| Sodium Citrate | 1.0 | Buffering | 6132-04-3 |
| Lecithin | 1 | Carrier encapsulation formulary* | 8002-43-5 |
| Sphingomyeline | 2 | Carrier encapsulation formulary* | 85187-10-6 |
| Linolenic Acid | 1 | Carrier encapsulation formulary* | 463-40-1 |
| Linoleic Acid | 1 | Carrier encapsulation formulary* | 60-33-3 |
| Phosphatidylcholin | 3 | Carrier encapsulation formulary* | 26853-31-6 |
| Caprylic Triglyceride | 1 | Carrier encapsulation formulary* | 73398-61-5 |
| Capric Triglyceride | 1 | Carrier encapsulation formulary* | 65381-09-1 |

TABLE 7-continued

| Ingredients (INCI) | Quantity wt % | Function | CAS-No. |
|---|---|---|---|
| VP/Eicosene Copolymer | 2.5 | Film forming | 28211-18-9 |
| Fillagrine trans-Urocanin Acide | 1 | UV-filter | 104-98-3-3465-72-3 |
| Butyl Methoxydibenzoylmethane Neo Heliopan 357, Eusolex 9020, Parsol 1789 | 3.8 | UV Filter | 70356-09-1 |
| Methylene Bis-Benzotriazolyl Tetramethylbutylphenol (nano) Tinosorb M | 2.5 | UV Filter | 103597-45-1 |
| Ethylhexyl Triazone Uvinul T 150 | 2.0 | UV Filter | 88122-99-0 |
| Bis-Ethylhexyloxyphenol Methoxyphenyl Triazine Tinosorb S | 0.8 | UV Filter | 187393-00-6 |
| Ethylhexyl Methoxycinnamate Uvinul MC 80, Parsol MCX, Neo Heliopan AV 4 | 0.1 | UV Filter | 5466-77-3 |
| Peroxyethanol | 3 | Conservant | 95684-29-0 |
| Total: | 100.000 | | |

Example 5 with UV-Filter System Body

TABLE 8

| Ingredients (INCI) | Quantity wt % | Function | CAS-No. |
|---|---|---|---|
| 7-DHC | 0.15 | Active ingredient ROS binder | 434-16-2 |
| HA* | 3 | Active ingredient Humectant | 9004-61-9 |
| Retinyl Palmitate | 0.2 | Skin Conditioning | 79-81-2 |
| Riboflavin | 0.1 | Skin Conditioning | 83-88-5 |
| Niacinamide | 2.0 | Skin Conditioning | 98-92-0 |
| Dexpanthenol | 2.5 | Skin Conditioning | 81-13-0 |
| Folic acid | 0.05 | Skin Conditioning | 59-30-3 |
| L-ascorbic acid | 2.0 | Skin Conditioning | 50-81-7 |
| Tocopheryl Acetate | 1.0 | Skin Conditioning | 7695-91-2 |
| Aqua destillata | 56.263 | Solvent | 7732-18-5 |
| Stearic Acid | 1.0 | Surfactant | 57-11-44 |
| Pyridoxine HCL | 3.0 | Conditioning Conservant | 8007-69-0/ 90320-37-9 |
| Sodium Ascorbyl Phosphate | 2.0 | Conditioning Conservant | 66170-10-3 |
| Polidocanol | 3.0 | Emulsifying Emolient | 3055-99-0 |
| Sodium Citrate | 1.0 | Buffering | 6132-04-3 |
| Lecithin | 1 | Carrier encapsulation formulary* | 8002-43-5 |
| Sphingomyeline | 2 | Carrier encapsulation formulary* | 85187-10-6 |
| Linolenic Acid | 1 | Carrier encapsulation formulary* | 463-40-1 |
| Linoleic Acid | 1 | Carrier encapsulation formulary* | 60-33-3 |

TABLE 8-continued

| Ingredients (INCI) | Quantity wt % | Function | CAS-No. |
|---|---|---|---|
| Phosphatidylcholin | 3 | Carrier encapsulation formulary* | 26853-31-6 |
| Caprylic Triglyceride | 1 | Carrier encapsulation formulary* | 73398-61-5 |
| Capric Triglyceride | 1 | Carrier encapsulation formulary* | 65381-09-1 |
| VP/Eicosene Copolymer | 2.5 | Film forming | 28211-18-9 |
| Trisodium Ethylenediamine Disuccinate Trisodium Ethylenediamine Disuccinate Solution, Natrlquest E30 3) | 0.037 | Chelating | 20846-91-7/ 178949-82-1 |
| Fillagrine trans-Urocanin Acide | 1 | UV-filter | 104-98-3-3465-72-3 |
| Butyl Methoxydibenzoylmethane Neo Heliopan 357, Eusolex 9020, Parsol 1789 | 3.8 | UV Filter | 70356-09-1 |
| Methylene Bis-Benzotriazolyl Tetramethylbutylphenol (nano) Tinosorb M | 2.5 | UV Filter | 103597-45-1 |
| Ethylhexyl Triazone Uvinul T 150 | 2.0 | UV Filter | 88122-99-0 |
| Bis-Ethylhexyloxyphenol Methoxyphenyl Triazine Tinosorb S | 0.8 | UV Filter | 187393-00-6 |
| Ethylhexyl Methoxycinnamate Uvinul MC 80, Parsol MCX, Neo Heliopan AV 4 | 0.1 | UV Filter | 5466-77-3 |
| Total: | 100.000 | | |

REFERENCES

1. Gary J. Fisher, Ph.D., Zeng Quan Wang, Ph.D., Subhash C. Datta, Ph.D james Varani, Ph.D., Sewonkang, M. D., And John J. Voorhees, M. D. Pathophysiology Of Premature Skin Aging Induced by Ultraviolet Light The New England Journal Of Medicine Dec. 11, 2016
2. Wound Repair and Regeneration. 15 (5): 708-17 September 2007.
3. American Academy of Dermatology, Aging Skin Net, "Causes of Aging Skin".
4. Matthias Wacker and Michael F. Holick Sunlight and Vitamin D A global perspective for health Dermato-Endocrinology 5:1, 51-108; January/February/March 2013.
5. Holick M F Vitamin D deficiency". N. Engl. J. Med. 357 (3): 266-81 July 2007.
6. Holick M F Vitamin D: the underappreciated D-lightful hormone that is important for skeletal and cellular health. Current Opinion in Endocrinology, Diabetes and Obesity. 9 (1): 87-98 February 2002.
7. Holick M F Sunlight and Vitamin D. Journal of General Internal Medicine. 17 (9): 733-735 September 2002.
8. Meghan Russell Assessing the Relationship between Vitamin D3 and Stratum Corneum Hydration for the Treatment of Xerotic Skin Nutrients 2012, 4, 1213-1218
9. Abramovits W. Calcitriol 3 microg/g ointment: an effective and safe addition to the armamentarium in topical psoriasis therapy. J Drugs Dermatol. 2009; 8(8 Suppl): s17-22.
10. Gerritsen M J, Van De Kerkhof P C, Langner A. Long-term safety of topical calcitriol 3 microg g(-1) ointment. Br J Dermatol. 2001; 144 Suppl 58:17-19.

11. Meghan Russell Assessing the Relationship between Vitamin D3 and Stratum Corneum Hydration for the Treatment of Xerotic Skin Johnson and Johnson Skin Research Center, CPPW, Johnson & Johnson Consumer Companies, Inc., Skillman, NJ 08558, USA Nutrients 2012, 4, 1213-1218
12. Rizova E, Corroller M. Topical calcitriol—studies on local tolerance and systemic safety. Br J Dermatol. 2001; 144 Suppl 58:3-10.
13. Mason A R, Mason J, Cork M, Dooley G, Edwards G. Topical treatments for chronic plaque psoriasis. Cochrane Database Syst Rev. 2009(2):CD005028.
14. Murphy G, Reich K. In touch with psoriasis: topical treatments and current guidelines. J Eur Acad Dermatol Venereol. 2011; 25 Suppl 4:3-8.
15. vY. Oda, Y. Uchida, S. Moradian, D. Crumrine, P. M. Elias, D. D. BikleVitamin D receptor and coactivators SRC 2 and 3 regulate epidermis-specific sphingolipid production and permeability barrier formation. J Invest Dermatol, 129 (2009), pp. 1367-1378
16. Jürgen Schauber, Richard L. Gallo, Antimicrobial peptides and the skin immune defense system, Journal of Allergy and Clinical Immunology, Volume 122, Issue 2, August 2008, Pages 261-266, ISSN 0091-6749
17. Burkiewicz C J, Guadagnin F A, Skare T L, do Nascimento M M, Servin S C, de Souza G D. Vitamin D and skin repair: a prospective, double-blind and placebo controlled study in the healing of leg ulcers. Rev Col Bras Cir. 2012 September-October; 39(5):401-7.
18. Schauber J, Dorschner R A, Coda A B, et al. Injury enhances TLR2 function and antimicrobial peptide expression through a vitamin D-dependent mechanism. J Clin Invest. 2007; 117:803-11.
19. Zasloff M. Sunlight, vitamin D, and the innate immune defenses of the human skin. J Invest Dermatol. 2005; 125:xvi-xvii.
20. J. D. Heilborn, M. F. Nilsson, G. Kratz, G. Weber, O. Sørensen, N. Borregaard, et al. The cathelicidin antimicrobial peptide LL-37 is involved in re-epithelialization of human skin wounds and is lacking in chronic ulcer epithelium J Invest Dermatol, 120 (2003), pp. 379-389.
21. De Haes P, Garmyn M, Verstuyf A et al. Two 14-epi analogues of 1,25-dihydroxyvitamin D3 protect human keratinocytes against the effects of UVB. Arch Dermatol Res 2004:12:527-534
22. De Haes P, Garmyn M, Carmeliet G et al. Molecular pathways involved in the anti-apoptotic effect of 1,25-dihydroxyvitamin D3 in primary human keratinocytes. J Cell Biochem 2004: 93: 951-967.
23. De Haes P, Garmyn M, Degreef H, Vantieghem K, Bouillon R, Sega-ert S. 1,25-Dihydroxyvitamin D3 inhibits ultraviolet B-induced apop-tosis, Jun kinase activation, and interleukin-6 production in primary human keratinocytes. J Cell Biochem 2003: 89: 663-673.
24. Wong G, Gupta R, Dixon K M et al. 1,25-Dihydroxyvitamin D and three low-calcemic analogs decrease UV-induced DNA damage via the rapid response pathway. J Steroid Biochem Mol Biol 2004: 89-90: 567-570.
25. De Haes P, Garmyn M, Verstuyf A et al. 1,25-Dihydroxyvitamin D3 and analogues protect primary human keratinocytes against UVB-induced DNA damage. J Photochem Photobiol B 2005: 78: 141-148
26. Reichrath, Jorg. Vitamin D and the skin: an ancient friend, revisited. Experimental dermatology, 2007, 16. Jg., Nr. 7, S. 618-625
27. Kielty C M, Whittaker S P, Grant M E, Shuttleworth C A. Type VI collagen microfibrils: evidence for a structural association with hyaluronan. J Cell Biol. 1992; 118:979-90
28. Baccarani-Contri M, Vincenzi D, Cicchetti F, Mori G, Pasquali-Ronchetti I. Immunocytochemical localization of proteoglycans within normal elastin fibers. Eur J Cell Biol. 1990; 53:305-12
29. Cleland R L, Wang J L. Ionic polysaccharides. 3. Dilute solution properties of hyaluronic acid fractions. Biopolymers. 1970; 9:799-810
30. Bhattacharya J, Cruz T, Bhattacha-rya S, Bray B A. Hyaluronan affects extravascular water in lungs of unanesthetized rabbits. J Appl Physiol. 1989; 66:2595-9
31. Weindl G, Schaller M, Schafer-Korting M, Korting H C. Hyaluronic acid in the treatment and prevention of skin diseases: molecular biological, pharmaceutical and clinical aspects. Skin Pharmacol Physiol. 2004; 17:207-13
32. Turino G M. The lung parenchyma—a dynamic matrix. (J. Burns Amberson lecture). Am Rev Respir Dis. 1985; 132:1324-34
33. Robert A. Greenwald And Wai W. Moy Effect Of Oxygen-Derived Free Radicals On Hyaluronic Acid Arthritis And Rheumatism, Vol. 23, No. 4 (April 1980)
34. Eleni Papakonstantinou, Michael Roth and George Karakiulakis Hyaluronic acid A key molecule in skin aging. Dermato-Endocrinology 4:3, 253-258; July-December 2012.
35. Foschi D1, Castoldi L, Radaelli E, Abelli P, Calderini G, Rastrelli A, Mariscotti C, Marazzi M, Trabucchi E. Hyaluronic acid prevents oxygen free-radical damage to granulation tissue: a study in rats. Int J Tissue React. 1990; 12(6):333-9.
36. Celebi S1, Tepe C, Yelken K, Celik O. Efficacy of dexpanthenol for pediatric post-tonsillectomy pain and wound healing. Ann Otol Rhinol Laryngol. 2013 July; 122(7):464-7.
37. Siddharth Mukherjee, Abhijit Date, Vandana Patravale, Hans Christian Korting, Alexander Roeder, Gunther Weindl Retinoids in the treatment of skin aging: an overview of clinical efficacy and safety Clinical Interventions in Aging 2006:1(4) 327-348.
38. Wohlrab J1, Kreft D. Niacinamide-mechanisms of action and its topical use in dermatology. Skin Pharmacol Physiol. 2014; 27(6):311-5.
39. Biro K1, Thaçi D, Ochsendorf F R, Kaufmann R, Boehncke W H. Efficacy of dexpanthenol in skin protection against irritation: a double-blind, placebo-controlled study. Contact Dermatitis. 2003 August; 49(2):80-4.
40. Julia Steitz, Jürgen Bruck, Julia Lenz, Steffi Bilchs, Thomas Tüting. Peripheral CD8+ T Cell Tolerance Against Melanocytic Self-Antigens in the Skin Is Regulated in Two Steps by CD4+ T Cells and Local Inflammation: Implications for the Pathophysiology of Vitiligo. Journal of Investigative Dermatology Volume 124, Issue 1, January 2005, Pages 144-150.
41. Knott A1, Koop U, Mielke H, Reuschlein K, Peters N, Muhr G M, Lenz H, Wensorra U, Jaspers S, Kolbe L, Raschke T, Stab F, Wenck H, Gallinat S. A novel treatment option for photoaged skin. J Cosmet Dermatol. 2008 March; 7(1):15-22.
42. The American Society of Health-System Pharmacists. Retrieved 8 Dec. 2016.
43. WHO Model Formulary 2008 (PDF). World Health Organization. 2009. p. 496. ISBN 9789241547659. Retrieved 8 Dec. 2016.

44. Prockop D J, Kivirikko K I (1995). "Collagens: molecular biology, diseases, and potentials for therapy". Annu. Rev. Biochem. 64: 403-34.
45. Peterkofsky B (December 1991). "Ascorbate requirement for hydroxylation and secretion of procollagen: relationship to inhibition of collagen synthesis in scurvy". Am. J. Clin. Nutr. 54 (6 Suppl): 1135S-1140S.
46. Kivirikko K I, Myllylä R (1985). "Post-translational processing of procollagens". Annals of the New York Academy of Sciences. 460: 187-201.
47. Rebouche C J (December 1991). "Ascorbic acid and carnitine biosynthesis". Am. J. Clin. Nutr. 54 (6 Suppl): 1147S-1152S. PMID 1962562.
48. Dunn W A, Rettura G, Seifter E, Englard S (September 1984). "Carnitine biosynthesis from gamma-butyrobetaine and from exogenous protein-bound 6-N-trimethyl-L-lysine by the perfused guinea pig liver. Effect of ascorbate deficiency on the in situ activity of gamma-butyrobetaine hydroxylase" (PDF). J. Biol. Chem. 259 (17): 10764-70. PMID 6432788.
49. Padayatty S J, Katz A, Wang Y, Eck P, Kwon O, Lee J H, Chen S, Corpe C, Dutta A, Dutta S K, Levine M (February 2003). "Vitamin C as an antioxidant: evaluation of its role in disease prevention". J Am Coll Nutr. 22 (1): 18-35. doi:10.1080/07315724.2003.10719272. PMID 12569111. Archived from the original on Jul. 21, 2010.
50. Traber M G, Stevens J F; Stevens (2011). "Free Radical Biology and Medicine—Vitamins C and E: Beneficial effects from a mechanistic perspective". Free Radical Biology and Medicine. 51 (5): 1000-13 2011.

The invention claimed is:
1. A method for preparing a homogeneous, stable liposomal hydrogel comprising the steps of:
   a) dispersing dried phospholipids at room temperature in a first aqueous solution to obtain phospholipid colloids;
   b) dispersing separately hyaluronic acid at room temperature in a second aqueous solution, wherein the hyaluronic acid is a mixture of low molecular, medium molecular, and high molecular weight hyaluronic acid;
   c) liquifying 7-dehydrocholesterol (7-DHC) at a temperature between 14° and 150° C.;
   d) adding an organic solvent to the liquified 7-DHC obtained in step c) to obtain a mixture;
   e) admixing the mixture obtained in step d) to the phospholipid colloids obtained in step a) under stirring at room temperature to obtain colloidal spheres of 20-150 nm;
   f) adding the dispersed hyaluronic acid obtained in step b) to the colloidal spheres of step e) to obtain a further mixture; and
   g) continue stirring the further mixture at room temperature to obtain a homogeneous, stable liposomal hydrogel comprising the 7-DHC and the mixture of hyaluronic acids encapsulated in phospholipid colloids.
2. The method according to claim 1, wherein 7-DHC is present at a concentration of 0.01 to 0.5 wt %.
3. The method according to claim 1, wherein the mixture of hyaluronic acid is present at a concentration of 0.01 to 8 wt %.
4. The method according to claim 1 wherein the organic solvent is propylene glycol.
5. The method according to claim 1 wherein in step (g) stirring is carried out for 20 minutes.
6. The method according to claim 1 wherein the homogeneous, stable liposomal hydrogel further comprises one or more further components selected from a vitamin A added at step d), at least one vitamin B added at step b), a vitamin C added at step b), and a vitamin E added at step d).
7. The method according to claim 6 wherein the homogeneous, stable liposomal hydrogel further comprises the at least one vitamin B added at step b), selected from riboflavin (vitamin B2), niacinamide (vitamin B3), dexpanthenol (Provitamin B5), and/or folic acid (vitamin B9).
8. The method according to claim 1 wherein the homogeneous, stable liposomal hydrogel further comprises i) retinyl palmitate (vitamin A), (ii) riboflavin (vitamin B2), (iii) niacinamide (vitamin B3), (iv) dexpanthenol (Provitamin B5), (v) folic acid (vitamin B9), (vi) L-ascorbic acid (vitamin C) and (vii) tocopheryl acetate (vitamin E), added at step d).
9. The method according to claim 1 wherein the homogeneous, stable liposomal hydrogel further comprises at least one UV-filter added at step b) or step d).
10. The method according to claim 1 wherein the homogeneous, stable liposomal hydrogel further comprises at least one adjuvant selected from the group consisting of surfactants, emulsifying agents, emollients, thickening agents, conditioning conservants, buffering agents, humectants, and perfuming agents, each added at step b) or step d).
11. The method according to claim 10 wherein the homogeneous, stable liposomal hydrogel further comprises the surfactant added at step b) or step d), selected from a polysorbate, a polycarbonate, polyvinylpyrrolidon (PVP), polyvidon, ovidonmembranes, povidone, copovidone, hypromellose or Eudragit EPO.
12. A liposomal hydrogel obtained according to a method of claim 1.
13. The liposomal hydrogel according to claim 12 further comprising one or more further components selected from a vitamin A, at least one vitamin B, a vitamin C, and a vitamin E.
14. The liposomal hydrogel according to claim 13 including the at least one vitamin B, wherein the at least one vitamin B is riboflavin (vitamin B2), niacinamide (vitamin B), dexpanthenol (Provitamin B5), and/or folic acid (vitamin B9).
15. The liposomal hydrogel according to claim 12 further comprising i) retinyl palmitate (vitamin A), (ii) riboflavin (vitamin B2), (iii) niacinamide (vitamin B3), (iv) dexpanthenol (Provitamin B5), (v) folic acid (vitamin B9), (vi) L-ascorbic acid (vitamin C) and (vii) tocopheryl acetate (vitamin E).
16. The liposomal hydrogel according to claim 12 further comprising at least one UV-filter.
17. The liposomal hydrogel according to claim 12 further comprising at least one adjuvant selected from the group consisting of surfactants, emulsifying agents, emollients, thickening agents, conditioning conservants, buffering agents, humectants, and perfuming agents.
18. The liposomal hydrogel according to claim 17 including the surfactant, wherein the surfactant is a polysorbate, polycarbonate, polyvinylpyrrolidon (PVP), polyvidon, ovidonmembranes, povidone, copovidone, hypromellose or Eudragit EPO.
19. The method according to claim 1 further comprising adding to the liquified at least one vitamin D3 or derivative thereof obtained in step c) a lipophilic agent selected from a vitamin A or a vitamin E.
20. The method according to claim 1 further comprising dispersing with the hyaluronic acid in the second aqueous solution a hydrophilic agent selected from a vitamin B or vitamin C.

* * * * *